(12) United States Patent
Willard (10) Patent No.: US 10,398,501 B2
(45) Date of Patent: Sep. 3, 2019

(54) ABLATION SYSTEMS INCLUDING PULSE RATE DETECTOR AND FEEDBACK MECHANISM AND METHODS OF USE

(71) Applicant: St. Jude Medical, Cardiology Division, Inc., St. Paul, MN (US)

(72) Inventor: Steven Willard, Bloomington, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 363 days.

(21) Appl. No.: 14/626,484

(22) Filed: Feb. 19, 2015

(65) Prior Publication Data

US 2015/0305806 A1    Oct. 29, 2015

Related U.S. Application Data

(60) Provisional application No. 61/983,623, filed on Apr. 24, 2014.

(51) Int. Cl.
*A61B 18/14* (2006.01)
*A61B 17/00* (2006.01)
*A61B 18/00* (2006.01)

(52) U.S. Cl.
CPC ........... *A61B 18/1492* (2013.01); *A61B 2017/00044* (2013.01); *A61B 2018/00404* (2013.01);
(Continued)

(58) Field of Classification Search
CPC .. A61B 2017/00044; A61B 2017/1204; A61B 2019/54; A61B 18/1492;
(Continued)

(56) References Cited

U.S. PATENT DOCUMENTS 3,650,277 A    3/1972 Sjostrand et al.
4,658,819 A    4/1987 Harris et al.
(Continued)

FOREIGN PATENT DOCUMENTS

WO    97/45157    12/1997
WO    00/66020    11/2000
(Continued)

OTHER PUBLICATIONS

Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
(Continued)

*Primary Examiner* — Michael F Peffley
*Assistant Examiner* — Tigist S Demie
(74) *Attorney, Agent, or Firm* — Armstrong Teasdale LLP (57) ABSTRACT

Methods, systems, and apparatuses for performing a renal denervation procedure using an ablation catheter are described. An ablation catheter system may include an ablation catheter including at least one electrode, a generator, and a pulse rate detector and feedback mechanism in electrical connection with the generator. In one embodiment, a method for controlling the temperature of a lesion created inside of a patient includes determining the pulse rate of the patient prior to, and optionally during, a renal denervation procedure and adjusting the amount of energy distributed to an ablation catheter electrode based at least in part on the pulse rate of the patient so as to control the temperature of the lesion being created. By controlling the temperature of the lesion during the ablation process, more consistent patient outcomes may be provided.

9 Claims, 2 Drawing Sheets

(52) U.S. Cl.
CPC ............ *A61B 2018/00434* (2013.01); *A61B 2018/00511* (2013.01); *A61B 2018/00577* (2013.01); *A61B 2018/00642* (2013.01); *A61B 2018/00714* (2013.01); *A61B 2018/00821* (2013.01); *A61B 2018/00839* (2013.01)

(58) Field of Classification Search
CPC ........... A61B 2018/00404; A61B 2018/00434; A61B 2018/00511; A61B 2018/00577; A61B 2018/00642; A61B 2018/00714; A61B 2018/00821; A61B 2018/00839
See application file for complete search history.

(56) References Cited

U.S. PATENT DOCUMENTS

| | | | |
|---|---|---|---|
| 5,035,694 A | 7/1991 | Kasprzyk et al. | |
| 5,255,679 A | 10/1993 | Imran | |
| 5,300,068 A | 4/1994 | Rosar et al. | |
| 5,368,591 A | 11/1994 | Lennox et al. | |
| 5,387,233 A | 2/1995 | Alferness et al. | |
| 5,465,717 A | 11/1995 | Imran et al. | |
| 5,531,779 A | 7/1996 | Dahl et al. | |
| 5,598,848 A | 2/1997 | Swanson et al. | |
| 5,607,462 A | 3/1997 | Imran | |
| 5,628,313 A | 5/1997 | Webster, Jr. | |
| 5,676,662 A | 10/1997 | Fleischhacker et al. | |
| 5,707,400 A | 1/1998 | Terry, Jr. et al. | |
| 5,769,077 A | 6/1998 | Lindegren | |
| 5,772,590 A | 6/1998 | Webster, Jr. | |
| 5,893,885 A | 4/1999 | Webster, Jr. | |
| 5,897,553 A | 4/1999 | Mulier et al. | |
| 5,954,649 A | 9/1999 | Chia et al. | |
| 5,954,719 A * | 9/1999 | Chen ................ | A61B 18/1206 606/34 |
| 6,004,269 A | 12/1999 | Crowley et al. | |
| 6,012,457 A | 1/2000 | Lesh | |
| 6,016,437 A | 1/2000 | Tu et al. | |
| 6,024,740 A | 2/2000 | Lesh et al. | |
| 6,073,048 A | 6/2000 | Kieval et al. | |
| 6,096,037 A | 8/2000 | Mulier et al. | |
| 6,117,101 A | 9/2000 | Diederich et al. | |
| 6,161,543 A | 12/2000 | Cox et al. | |
| 6,178,349 B1 | 1/2001 | Kieval | |
| 6,200,312 B1 | 3/2001 | Zikorus et al. | |
| 6,216,044 B1 | 4/2001 | Kordis | |
| 6,233,491 B1 | 5/2001 | Kordis et al. | |
| 6,283,951 B1 | 9/2001 | Flaherty et al. | |
| 6,287,608 B1 | 9/2001 | Levin et al. | |
| 6,292,695 B1 * | 9/2001 | Webster, Jr. ......... | A61N 1/0563 607/113 |
| 6,322,559 B1 | 11/2001 | Daulton et al. | |
| 6,460,545 B2 | 10/2002 | Kordis | |
| 6,522,926 B1 | 2/2003 | Kieval et al. | |
| 6,532,388 B1 * | 3/2003 | Hill ..................... | A61N 1/0517 607/2 |
| 6,613,045 B1 | 9/2003 | Laufer et al. | |
| 6,616,624 B1 | 9/2003 | Kieval | |
| 6,635,054 B2 | 10/2003 | Fjield et al. | |
| 6,656,174 B1 | 12/2003 | Hedge et al. | |
| 6,669,655 B1 | 12/2003 | Acker et al. | |
| 6,699,231 B1 | 3/2004 | Sterman et al. | |
| 6,748,255 B2 | 6/2004 | Fuimaono et al. | |
| 6,805,131 B2 | 10/2004 | Kordis | |
| 6,845,267 B2 | 1/2005 | Harrison et al. | |
| 6,954,977 B2 | 10/2005 | Maguire et al. | |
| 6,970,730 B2 | 11/2005 | Fuimaono et al. | |
| 7,122,031 B2 | 10/2006 | Edwards et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,245,955 B2 | 7/2007 | Rashidi | |
| 7,291,146 B2 | 11/2007 | Steinke et al. | |
| 7,363,076 B2 | 4/2008 | Yun et al. | |
| 7,419,486 B2 | 9/2008 | Kampa | |
| 7,465,288 B2 | 12/2008 | Dudney et al. | |
| 7,468,062 B2 | 12/2008 | Oral et al. | |
| 7,481,803 B2 | 1/2009 | Kesten et al. | |
| 7,653,438 B2 | 1/2010 | Deem et al. | |
| 7,717,948 B2 | 5/2010 | Demarais et al. | |
| 7,742,795 B2 | 6/2010 | Stone et al. | |
| 7,850,685 B2 | 12/2010 | Kunis et al. | |
| 7,949,407 B2 | 5/2011 | Kaplan et al. | |
| 8,145,316 B2 | 3/2012 | Deem et al. | |
| 8,224,416 B2 | 7/2012 | de la Rama et al. | |
| 8,343,213 B2 | 1/2013 | Salahieh et al. | |
| 8,347,891 B2 | 1/2013 | Demarais et al. | |
| 8,442,639 B2 | 5/2013 | Walker et al. | |
| 8,454,594 B2 | 6/2013 | Demarais et al. | |
| 8,545,495 B2 | 10/2013 | Scheib | |
| 9,022,948 B2 | 5/2015 | Wang | |
| 2002/0068885 A1 | 6/2002 | Harhen et al. | |
| 2002/0120304 A1 | 8/2002 | Mest | |
| 2003/0050681 A1 | 3/2003 | Pianca et al. | |
| 2003/0060858 A1 | 3/2003 | Kieval et al. | |
| 2003/0074039 A1 | 4/2003 | Puskas | |
| 2003/0114739 A1 | 6/2003 | Fuimaono et al. | |
| 2003/0216792 A1 | 11/2003 | Levin et al. | |
| 2003/0233099 A1 | 12/2003 | Danaek et al. | |
| 2004/0215186 A1 | 10/2004 | Cornelius et al. | |
| 2005/0288730 A1 | 12/2005 | Deem et al. | |
| 2006/0089678 A1 | 4/2006 | Shalev | |
| 2007/0135875 A1 | 6/2007 | Demarais et al. | |
| 2008/0255478 A1 | 10/2008 | Burdette | |
| 2009/0076409 A1 | 3/2009 | Wu et al. | |
| 2009/0149848 A1 * | 6/2009 | Werneth ............. | A61B 18/1492 606/33 |
| 2010/0016762 A1 | 1/2010 | Thapliyal et al. | |
| 2010/0094209 A1 | 4/2010 | Drasler et al. | |
| 2010/0106033 A1 * | 4/2010 | Lian ................... | A61B 5/02405 600/509 |
| 2010/0168737 A1 | 7/2010 | Grunewald | |
| 2010/0249773 A1 | 9/2010 | Clark et al. | |
| 2010/0268307 A1 | 10/2010 | Demarais et al. | |
| 2010/0286684 A1 | 11/2010 | Hata et al. | |
| 2011/0004087 A1 | 1/2011 | Fish et al. | |
| 2011/0118726 A1 | 5/2011 | de la Rama et al. | |
| 2011/0137298 A1 | 6/2011 | Nguyen et al. | |
| 2011/0160720 A1 | 6/2011 | Johnson | |
| 2011/0190755 A1 * | 8/2011 | Mathur ............. | A61B 18/1233 606/33 |
| 2011/0213231 A1 | 9/2011 | Hall et al. | |
| 2011/0257641 A1 | 10/2011 | Hastings et al. | |
| 2011/0264011 A1 | 10/2011 | Wu et al. | |
| 2011/0264086 A1 | 10/2011 | Ingle | |
| 2011/0307034 A1 | 12/2011 | Hastings et al. | |
| 2012/0143097 A1 | 6/2012 | Pike, Jr. | |
| 2012/0143298 A1 | 6/2012 | Just et al. | |
| 2012/0265198 A1 | 10/2012 | Crow et al. | |
| 2012/0296232 A1 | 11/2012 | Ng | |
| 2012/0323233 A1 | 12/2012 | Maguire et al. | |
| 2013/0116737 A1 | 5/2013 | Edwards et al. | |
| 2013/0131743 A1 | 5/2013 | Yamasaki et al. | |
| 2013/0144251 A1 | 6/2013 | Sobotka | |
| 2013/0172715 A1 | 7/2013 | Just et al. | |
| 2013/0274614 A1 | 10/2013 | Shimada et al. | |
| 2014/0018788 A1 | 1/2014 | Engelman et al. | |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |

(56) References Cited

FOREIGN PATENT DOCUMENTS

| WO | 2012/064818 | 5/2012 |
|---|---|---|
| WO | 2012/106492 | 8/2012 |

OTHER PUBLICATIONS

Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of the American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.

Oparil, Suzanne et al, Renal Nerve Ablation: Emerging Role in Therapeutics; Blood Pressure, Oct. 2011, vol. 20, No. 5, pp. 253-255.
Oral, Hakan et al, Pulmonary Vein Isolation for Paroxysmal and Persistent Atrial Fibrillation, Circulation Journal of the American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, Time Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of the American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, Jan. 10-15, 2002.
Pearce, John A. et al, Blood Vessel Architectural Features and Their Effect on Thermal Phenomena, Critical Reviews, vol. CR75, , Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of the American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of the American Heart Association, 1999;99:319-325.
Plouin, Pierre-Francois et al, Blood Pressure Outcome of Angioplasty in Atherosclerotic Renal Artery Stenosis A Randomized Trial, Hypertension Journal of the American Heart Association, 1998;31:823-829.

(56) References Cited

OTHER PUBLICATIONS

Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
European Search Report for Application No. 15155826.9 dated Sep. 16, 2015.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of the American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of the American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of the American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.

Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Grassi, Guido et al, Baroreflex Control of Sympathetic Nerve Activity in Essential and Secondary Hypertension, Hypertension Journal of the American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of the American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6(4):270-6.
Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart 2013;0:1-9.

(56) References Cited

OTHER PUBLICATIONS

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Howell, Marcus H. et al, Tandem Stenting of Crossed Renal Arteries with Ostial Stenosis, Tex Heart Inst J. 2000; 27(2): 166-169.

Hoye, Neil A. et al, Endovascular Renal Denervation: A Novel Sympatholytic with Relevance to Chronic Kidney Disease, Clinical Kidney Journal Advance Access, (2013) 0: 1-8.

Huang, Shoei K. Stephen et al, Radiofrequency Catheter Ablation of Cardiac Arrhythmias, Basic Concepts and Clinical Applications, Wiley-Blackwell, Jun. 2000, 1-12.

Huang, Wann-Chu, Renal Denervation Prevents and Reverses Hyperinsulinemia-Induced Hypertension in Rats, Hypertension Journal of the American Heart Association, 1998;32:249-254.

Humpreys, Michael H., Renal Nerves and CKD: Is Renal Denervation the Answer?, Journal of the American Socity of Nephrology, 2012, 23: 1-3.

International Search Report and Written Opinion for Application No. PCT/US2010/054637 dated Jan. 3, 2011.

International Search Report and Written Opinion for Application No. PCT/US2010/054684 dated Jan. 10, 2011.

Irigoyen, M.C.C. et al, Baroreflex Control of Sympathetic Activity in Experimental Hypertension, Brazilian Journal of Medical and Biological Research, (1998) 31: 1213-1220.

Izzo, Jr, Joseph L. et al, The Sympathetic Nervous System and Baroreflexes in Hypertension and Hypotension, Current Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.

Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.

Jais, Pierre et al, Efficacy and Safety of Septal and Left-Atrial Linear Ablation for Atrial Fibrillation, The American Journal of Cardiology, vol. 84 (9A), Nov. 1999, 139R-146R.

Janssen, Ben J.A. et al, Frequency-Dependent Modulation of Renal Blood Flow by Renal Nerve Activity in Conscious Rabbits, American Journal of Physiology, 1997, 273:R597-R608.

Janssen, Ben J.A. et al, Renal Nerves in Hypertension, Miner Electrolyte Metab 1989;15:74-82.

Jin, Yu et al, No Support for Renal Denervation in a Meta-Analysis, JACC vol. 62, No. 21, 2013 Correspondence Nov. 19/26, 2013:2029-30.

Kaltenbach, Benjamin et al, Renal Artery Stenosis After Renal Sympathetic Denervation, J Am Coll Cardiol. Dec. 25, 2012;60(25):2694-5.

Kaltenbach, Benjamin et al, Renal Sympathetic Denervation as Second-Line Therapy in Mild Resistant Hypertension: A Pilot Study, Catheterization and Cardiovascular Interventions 81:335-339 (2013).

Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.

Kandzari, David E. et al, Catheter-Based Renal Denervation for Resistant Hypertension: Rationale and Design of the Symplicity HTN-3 Trial, Clin. Cardiol. 35, 9, 528-535 (2012).

Kapural, Leonardo et al, Radiofrequency Ablation for Chronic Pain Control, Current Pain and Headache Reports 2001, 5:517-525.

Kassab, Salah et al, Renal Denervation Attenuates the Sodium Retention and Hypertension Associated with Obesity, Hypertension vol. 25, No. 4, Part 2 Apr. 1995.

Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.

Katholi, Richard E. et al, Role of the Renal Nerves in the Pathogenesis of One-Kidney Renal Hypertension in the Rat, Hypertension. 1981;3:404-409.

Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.

Katritsis, Demosthenes et al, Recurrence of Left Atrium-Pulmonary Vein Conduction Following Successful Disconnection in Asymptomatic Patients, Europace (2004) 6, 425e432.

Killip III, Thomas, Oscillation of Blood Flow and Vascular Resistance During Mayer Waves, Circulation Research, vol. XI, Dec. 1962, 987-993.

Kingwell, Bronwyn A. et al, Assessment of Gain of Tachycardia and Bradycardia Responses of Cardiac Baroreflex, Am J Physiol Heart Circ Physiol 260:H1254-H1263, 1991.

Kirchheim, H. et al, Sympathetic Modulation of Renal Hemodynamics, Renin Release and Sodium Excretion, Klin Wochenschr (1989) 67: 858-864.

Klein, GE et al, Endovascular Treatment of Renal Artery Aneurysms with Conventional Non-Detachable Microcoils and Guglielmi Detachable Coils, Br J Urol. Jun. 1997; 79(6):852-860.

Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.

Koepke, John P. et al, Functions of the Renal Nerves, The Physiologist, vol. 28, No. 1, Feb. 1985, 47-52.

Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.

Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.

Krum, Henry et al, Device-Based Antihypertensive Therapy: Therapeutic Modulation of the Autonomic Nervous System, Circulation. 2011;123:209-215.

La Grange, Ronald G. et al, Selective Stimulation of Renal Nerves in the Anesthetized Dog: Effect on Renin Release During Controlled Changes in Renal Hemodynamics, Circulation Research, Journal of the American Heart Association, 1973;33:704-712.

Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.

Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.

Lambert, Gavin W. et al, Health-Related Quality of Life After Renal Denervation in Patients With Treatment-Resistant Hypertension, Hypertension. 2012;60:1479-1484.

Lee, Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

Leishman, A.W.D., Hypertension—Treated and Untreated, British Medical Journal, May 1959, 1361-1368.

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

(56) References Cited

OTHER PUBLICATIONS

Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After SYMPLICITY HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of the American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal but Not Cardiac Sympathetic Activity in Humans; Hypertension Journal of the American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65, 729-734.
Zazgornik, Jan et al, Bilateral Nephrectomy: The Best, but Often Overlooked, Treatment for Refractory Hypertension in Hemodialysis Patients, AJH 1998; 11:1364-1370.
Abboud, Francois M., The Sympathetic System in Hypertension, State-of-the-Art Review, Hypertension Journal of the American Heart Association, Hypertension 4 (suppl II): II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6(2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of the American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.

(56) References Cited

OTHER PUBLICATIONS

Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review—Part II, Journal of the National Medical Association, May 1948, vol. 40, No. 3., 113-116.
Dailey, U.G., Surgical Treatment of Hypertension: A Review—Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension a Systematic Review and Meta-Analysis, Journal of the American College of Cardiology, vol. 62, No. 3, 2013, 231-241.
De Wardener, H.E., The Hypothalamus and Hypertension, Physiological Reviews,vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F. et al, Neural Control of Renal Function: Cardiovascular Implications, Hypertension Journal of the American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of the American Heart Association, vol. 41, Mar. 2003, Part II, 621-624.

Robbins, Ivan M. et al, Pulmonary Vein Stenosis After Catheter Ablation of Atrial Fibrillation, Circulation Journal of the American Heart Association, 1998;98:1769-1775.
Rocha-Singh, Krishna J., Catheter-Based Sympathetic Renal Denervation a Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4):94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of the American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of the American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of the American Heart Association, 2001;37:1053-1059.
Stanley, James C., Surgical Treatment of Renovascular Hypertension, The American Journal of Surgery, vol. 174, Aug. 1997, 102-110.

(56) References Cited

OTHER PUBLICATIONS

Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of the American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following *KSR* V. *Teleflex*, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of the American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.—Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of the American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.

\* cited by examiner

ABLATION SYSTEMS INCLUDING PULSE RATE DETECTOR AND FEEDBACK MECHANISM AND METHODS OF USE

CROSS-REFERENCE TO RELATED APPLICATIONS

This application claims the benefit of U.S. Provisional Patent Application No. 61/983,623, filed Apr. 24, 2014, the entire specification of which is incorporated herein.

BACKGROUND OF THE DISCLOSURE

1. Field of the Disclosure

The present disclosure relates generally to methods, systems, and apparatuses for performing an ablation procedure. More particularly, the present disclosure relates to renal denervation methods, systems, and apparatuses that utilize a pulse rate detector and feedback mechanism generally in electrical connection with a generator to compensate for the pulse rate of a patient and to monitor and adjust the energy supplied to an ablation catheter to control the temperature at a lesion site within a desired range.

2. Background Art

It is known that various renal ablation procedures for the ablation of perivascular renal nerves have been used for the treatment of hypertension, and specifically for drug-resistant hypertension. Generally, one or more radiofrequency electrodes are introduced into the body and fed into the renal artery and used to ablate the efferent and afferent nerves that generally run the length of the artery. In some cases, a single ablation procedure may include six to ten or more ablation areas along and around the wall of the artery. Typically, the operator performing the procedure will ablate one discrete area of the artery and then move the ablation electrode a desired distance lengthwise about the length of the artery and also rotate the handle of the catheter to move the ablation electrode circumferentially around the artery. In some cases, the operator may move the ablation electrode circumferentially about 45 degrees around the artery wall between ablations. By varying the ablation treatment sites lengthwise down and circumferentially around the artery wall, any potential overall damage to the artery wall can be minimized or eliminated while the overall ablation of the efferent and afferent nerves can still be substantially complete and effective.

During the ablation procedure, the operator, typically a doctor, performing the procedure generally attempts to monitor and track all of the areas of the artery wall that have previously been ablated to avoid over-treatment of any one site. This monitoring and tracking should be done both along the length of the artery as well as around the circumference of the artery wall to ensure proper ablation of the arterial nerves and the best procedural results. Feedback to the operator is generally provided regarding the temperature at the ablation site, which can be indicative of the effectiveness of the ablation itself, and whether the nerve has been ablated.

BRIEF SUMMARY OF THE DISCLOSURE

In one aspect, the present disclosure is directed to an ablation catheter system for creating a lesion in a patient. The ablation catheter system comprises an ablation catheter including at least one electrode, a generator, and a pulse rate detector and feedback mechanism in electrical connection with the generator.

In another aspect, the present disclosure is directed to a method for controlling the temperature of a lesion created inside of a patient during an ablation procedure using an ablation catheter including at least one electrode. The method comprises: (i) creating the lesion while monitoring the pulse rate of the patient; and (ii) adjusting the energy supplied to the at least one ablation catheter electrode to create the lesion based on the pulse rate of the patient so as to control the temperature of the lesion.

Another aspect of the present disclosure is directed to a renal ablation method for creating a lesion in an artery of a patient. The method comprises: (i) determining a baseline pulse rate level of the patient; (ii) determining the amount of energy to be transmitted to an ablation catheter for creating the lesion at a desired temperature based in part on the baseline pulse rate level; (iii) creating the lesion while monitoring the temperature at the lesion and the pulse rate of the patient; and (iv) adjusting the amount of energy transmitted to the ablation catheter creating the lesion as needed to maintain the desired temperature of the lesion based in part on the pulse rate of the patient.

Another aspect of the present disclosure is directed to an ablation catheter system for creating a lesion in a patient. The ablation catheter system comprises a pulse rate detector and feedback mechanism in communication with a generator.

BRIEF DESCRIPTION OF THE DRAWINGS

Corresponding reference characters indicate corresponding parts throughout the drawings.

DETAILED DESCRIPTION OF THE DISCLOSURE

Many ablation systems, including both renal ablation systems and heart tissue ablation systems, use radio frequency (RF) energy to generate heat at a target tissue site to create a lesion and ablate undesirable tissue, including undesirable nerve paths and other tissue. The RF energy is typically delivered through an electrode located on an ablation catheter and positioned in an artery or vein. The temperature at the lesion site is controlled by a sensing thermocouple mounted in or around the electrode such that a temperature signal may be directed back to the RF energy source from the thermocouple, and the amount of energy transmitted to the ablation catheter controlled/adjusted as needed to provide the desired temperature. Because most electrodes are configured as electrode rings or rounded catheter tips, generally only about 25% or so of the electrode surface is in contact with the target tissue site, while the remainder of the electrode surface remains in the blood stream and not in contact with the tissue surface. The flow of the blood stream is controlled by the heart, which has a pulse rate typically measured in beats per minute.

It has now been discovered that the pulse rate of a patient may impact the temperature as read by the thermocouple (or other temperature monitoring device) at the site of the lesion creation; that is, the pulse rate of the patient may have a material effect and a direct correlation on the temperature measurement of the lesion being created in the target tissue. As the pulse rate increases, the lesion temperature increases. This is significant as patient pulse rates may vary greatly; that is, pulse rates may easily range between 60 beats per minute to 180 beats or more per minute. It has been found that as the pulse rate of the patient increases, the blood flow also increases at and around the ablation catheter and electrode; because a majority of the electrode on the ablation catheter is located in the blood stream and not in direct contact with the tissue surface as noted above, there is a cooling effect that occurs at the majority of the electrode surface in contact with the blood. When this cooling occurs, the thermocouple senses it and sends a cooler temperature reading to the generator (or other component of the ablation system that may control energy output to the ablation catheter) than what the temperature actually is at the tissue surface. As a result of the cooler temperature reading, the generator will increase the amount of energy sent to the ablation catheter to generate increased heat at the lesion formation site. As such, in some cases where a patient's pulse is changing throughout the course of a procedure, it may sometimes be difficult to keep the temperature at the lesion site constant in a desired range.

The present disclosure is generally directed to creating a lesion in a patient wherein the temperature of the lesion is controlled within a target range by compensating for the cooling/heating impact of a patient's blood flow on the ablation catheter electrode. More specifically, the present disclosure is directed to apparatuses, methods, and systems for detecting the pulse rate of a patient before and/or during the creation of a lesion inside of the patient's body and using the pulse rate to assist in determining the amount of energy that should be supplied by a generator to the ablation catheter to keep the temperature of the lesion being created within a desired range. Generally, a pulse rate detector, such as a finger-mounted pulse rate detector or the like, is used in combination with a feedback mechanism that is in electrical connection with the generator (or other suitable ablation system component) to control the amount of energy delivered to the ablation catheter electrode.

The various approaches described herein may allow an ablation catheter system to more accurately control the temperature of a lesion being created inside of a patient during a renal denervation procedure (or other ablation procedure) by compensating for the cooling/heating impact of the patient's blood flow on the ablation catheter electrode. This can reduce or eliminate any potential damage to the renal artery (or other area of the body) due to potential overheating at the lesion site and improve patient results by standardizing lesion outcomes. Additionally, the information may allow for improved overall procedure management and efficiency. These and other benefits of the disclosure are set forth in detail herein.

Figure 1:
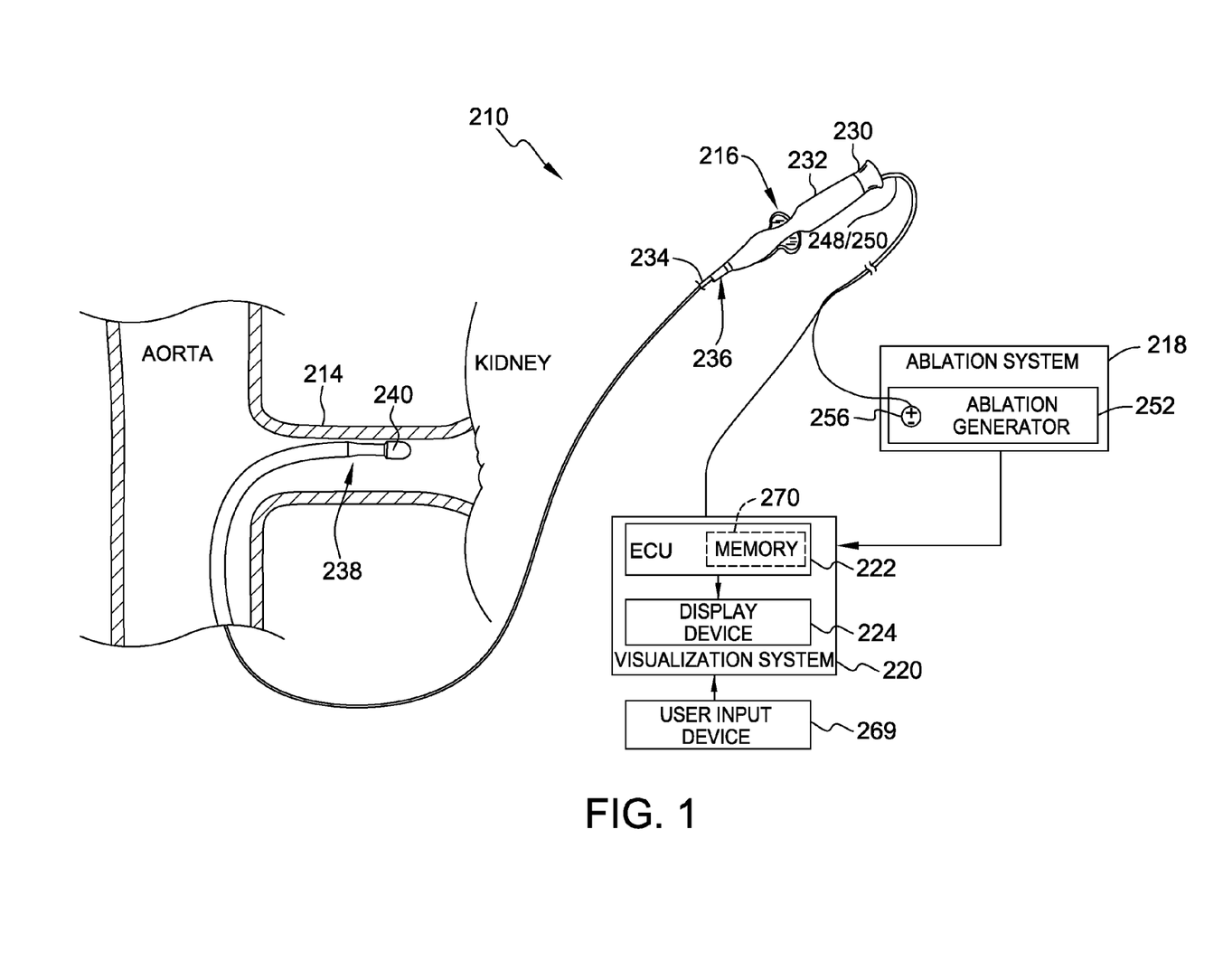
FIG. 1 is a diagrammatic view of a renal denervation system for presenting information relating to lesion formation in a renal artery in accordance with embodiments of the present disclosure.

Referring now to the Figures, FIG. 1 illustrates one exemplary embodiment of an ablation system 210 for performing one or more diagnostic and/or therapeutic functions that include components for presenting information representative of lesion formations in renal artery 214 during an ablation procedure performed thereon. It should be understood, however, that system 210 has equal applicability to ablation procedures on other tissues as well, including cardiac tissues.

Among other components, system 210 includes a medical device (such as, for example, catheter 216), ablation system 218, and system 220 for the visualization, navigation, and/or mapping of internal body structures. System 220 may include, for example and without limitation, an electronic control unit (ECU) 222, display device 224, user input device 269, and memory 270. Alternatively, ECU 222 and/or display device 224 may be separate and distinct from, but electrically connected to and configured for communication with, system 220.

With continued reference to FIG. 1, catheter 216 is provided for examination, diagnosis, and/or treatment of internal body tissues, such as renal artery 214. In an exemplary embodiment, catheter 216 comprises a radio frequency (RF) ablation catheter. It should be understood, however, that catheter 216 is not limited to an RF ablation catheter. Rather, in other embodiments, catheter 216 may comprise an irrigated catheter and/or other types of ablation catheters (e.g., cryoablation, ultrasound, balloon, basket, single electrode, bullet, etc.).

In an exemplary embodiment, catheter 216 is electrically connected to ablation system 218 to allow for the delivery of RF energy. Catheter 216 may include a cable connector or interface 230, handle 232, shaft 234 having a proximal end 236 and distal end 238 (as used herein, "proximal" refers to a direction toward the end of catheter 216 near the operator, and "distal" refers to a direction away from the operator and (generally) inside the body of a subject or patient), and one or more electrodes 240 mounted in or on shaft 234 of catheter 216. In an exemplary embodiment, electrode 240 is disposed at or near distal end 238 of shaft 234, with electrode 240 comprising an ablation electrode disposed at the extreme distal end 238 of shaft 234 for contact with renal artery 214. Catheter 216 may further include other conventional components such as, for example and without limitation, sensors, additional electrodes (e.g., ring electrodes) and corresponding conductors or leads, thermocouples, or additional ablation elements, e.g., a high intensity focused ultrasound ablation element and the like.

Connector 230 provides mechanical and electrical connection(s) for cables 248 and 250 extending from ablation system 218, and visualization, navigation, and/or mapping system 220. Connector 230 is conventional in the art and is disposed at the proximal end of catheter 216.

Handle 232 provides a location for the operator to hold catheter 216 and may further provide means for steering or guiding shaft 234 within renal artery 214. For example, handle 232 may include means to change the length of a guidewire extending through catheter 216 to distal end 238 of shaft 234 to steer shaft 234. Handle 232 is also conventional in the art and it will be understood that the construction of handle 232 may vary. In another exemplary embodiment, catheter 216 may be robotically driven or controlled. Accordingly, rather than an operator manipulating a handle to steer or guide catheter 216, and shaft 234 thereof, in particular, a robot is used to manipulate catheter 216.

Shaft 234 is generally an elongated, tubular, flexible member configured for movement within renal artery 214. Shaft 234 supports, for example and without limitation, electrode 240, associated conductors, and possibly additional electronics used for signal processing or conditioning. Shaft 234 may also permit transport, delivery and/or removal of fluids (including irrigation fluids, cryogenic ablation fluids, and bodily fluids), medicines, and/or surgical tools or instruments. Shaft 234 may be made from conventional materials such as polyurethane, and defines one or more lumens configured to house and/or transport at least electrical conductors, fluids, or surgical tools. Shaft 234 may be introduced into renal artery 214 through a conventional introducer. Shaft 234 may then be steered or guided through renal artery 214 to a desired location with guidewires or other means known in the art.

With further reference to FIG. 1, ablation system 218 is comprised of, for example, ablation generator 252. Ablation generator 252 generates, delivers, and controls RF energy output by ablation catheter 216 and electrode 240 thereof, in particular. In an exemplary embodiment, ablation generator 252 includes RF ablation signal source 256 configured to generate an ablation signal that is output across a pair of source connectors: a positive polarity connector SOURCE (+), which may be electrically connected to tip electrode 240 of catheter 216; and a negative polarity connector SOURCE (−). It should be understood that the term connectors as used herein does not imply a particular type of physical interface mechanism, but is rather broadly contemplated to represent one or more electrical nodes. Source 256 is configured to generate a signal at a predetermined frequency in accordance with one or more user specified parameters (e.g., power, time, etc.) and under the control of various feedback sensing and control circuitry as is known in the art. Source 256 may generate a signal, for example, with a frequency of about 450 kHz or greater. Ablation generator 252 may also monitor various parameters associated with the ablation procedure including, for example, impedance, the temperature at the distal tip of the catheter, applied ablation energy, and the position of the catheter, and provide feedback to the clinician or another component within system 210 regarding these parameters.

In accordance with the present disclosure, the ablation system described above may additionally include one or more pulse rate detectors and one or more feedback mechanisms to detect, measure, assess, monitor, and/or report the pulse rate of a patient undergoing an ablation procedure to create one or more lesions inside of the body, and particularly one or more ablations inside of a renal artery, to the ablation generator (or other suitable component) of the ablation system such that the target temperature for the electrode may be controlled and adjusted as necessary so that the lesion is created at a desired temperature. The pulse rate detector is generally connected electrically via the feedback mechanism to the generator that supplies the energy to the ablation catheter, and specifically to the one or more electrodes on the ablation catheter, such that the generator, upon receiving the pulse rate data of the patient, can determine the appropriate amount of energy to provide to the electrode or electrodes to maintain the temperature of the lesion in a desired range, which may be, for example, from about 60° C. to about 95° C., including from about 60° C. to about 85° C., including about 70° C. By monitoring the patient's pulse rate, the target temperature for the electrode (as measured by a thermocouple or other suitable temperature monitoring component of the ablation system) can be adjusted so that, for example, if the pulse rate is low, the target temperature for the electrode could be increased, whereas if the pulse rate is high, the target temperature for the electrode could be decreased such that the lesion being created is held at or near the desired temperature to improve the resulting quality and consistency thereof.

Suitable pulse rate detectors are known generally in the art and the exact pulse rate detector, including the exact size and configuration of the pulse rate detector, selected and utilized in the embodiments of the present disclosure is not critical. The pulse rate detector should be capable of detecting the pulse rate of a patient in a semi-continuous or continuous manner and reporting the pulse rate through a feedback mechanism or loop to another component for processing. Additionally, suitable feedback mechanisms or feedback loops are known generally in the art and the exact feedback mechanism or loop selected and utilized in the embodiments of the present disclosure is not critical. In one specific embodiment, the pulse rate detector may be sized and configured for attachment to the finger of the patient such that the pulse rate detector may "clip" onto the patient's finger and allow the pulse rate to be detected and measured and sent to the generator, or other component of the ablation system, as desired such that the pulse rate may be used to determine the energy requirements to be sent to the electrode(s) on the ablation catheter. In another specific embodiment, the pulse rate detector may be sized and configured for attachment to the wrist of the patient such that the pulse rate detector may attach onto the patient's wrist and allow the pulse rate to be detected and measured and sent to the generator, or other component of the ablation system, as desired such that the pulse rate may be used to determine the energy requirements to be sent to the electrode(s). In another specific embodiment, the pulse of the patient may be detected and measured and sent to the generator using an electrocardiogram (EKG) or other similar heart monitoring method or test. The pulse rate detector for use in the present disclosure as described herein may be attached to one or more other parts of the body within the scope of the present disclosure.

Figure 2:
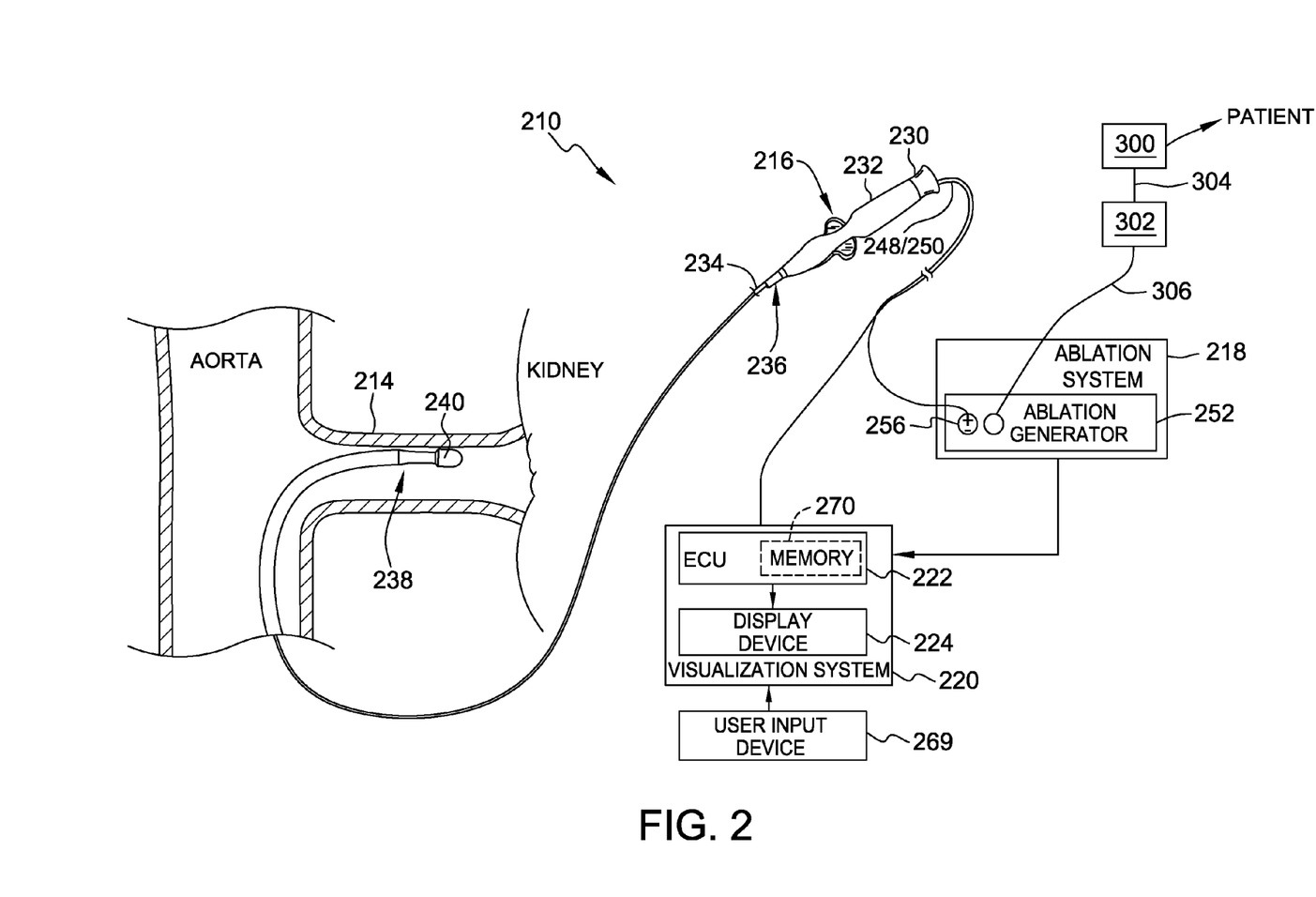
FIG. 2 is a diagrammatic view of a renal denervation system for presenting information relating to lesion formation in a renal artery in accordance with embodiments of the present disclosure that include a patient pulse rate detector and feedback mechanism.

Referring now to FIG. 2, there is shown the exemplary embodiment of the ablation system of FIG. 1 further including pulse rate detector 300, which is connected in a suitable manner to a patient as discussed herein, and feedback mechanism 302, which is connected to pulse rate detector 300 via electric connector wire 304 to receive patient pulse rate data for transmission to ablation generator 252 via connector wire 306. Although shown in FIG. 2 as being connected to ablation generator 252 via feedback mechanism 302 and electric connector wires 304 and 306, it is within the scope of the present disclosure for pulse rate detector 300 to communicate with ablation generator 252 (or another component of ablation system 210, such as a computer (not shown)), in a wireless manner such that pulse rate detector could optionally include feedback mechanism internally and provide pulse rate data to ablation generator 252 wirelessly, such as over a WIFI or similar network for data transmission. Also, although shown in FIG. 2 as being separate and distinct parts of ablation system 210, it is within the scope of the present disclosure for pulse rate detector 300 and feedback mechanism 302 to be a single, integrated unit connected to ablation generator 252 (or another component of ablation system 210) via an electric connector wire or wirelessly.

In one exemplary embodiment of the present disclosure, pulse rate detector 300 and feedback mechanism 302 are used in a renal denervation procedure (or other ablation procedure, such as, for example, cardiac ablation) to intermittently measure and/or record/report pulse rate data to ablation generator 252, and optionally, a renal denervation operator. The pulse rate of the patient can be intermittently monitored and the energy provided by ablation generator 252 to electrode 240 updated and controlled throughout the ablation procedure and the creation of one or more lesions to allow the temperature at the lesion creation site or sites to remain in a desired range; that is, pulse rate detector 300 and feedback mechanism 302 are used in an "on-again, off-again" process to provide pulse rate data to ablation generator 252 and optionally a system operator on a periodic, discontinuous basis. In one embodiment of this process, the operator may first determine a baseline pulse rate for the patient; that is, the operator may determine the pulse rate of the patient prior to any ablations being performed such that the operator (and ablation generator 252) has a baseline pulse rate from which to interpret future pulse rate readings. In other embodiments, a baseline pulse rate value may not be determined.

Once the baseline pulse rate of the patient has been determined, in some embodiments the operator may determine a target lesion temperature that is desired for the particular procedure; that is, a target lesion-creation temperature may be determined for the ablation system to obtain and maintain. The ablation system will then utilize the pulse rate data supplied to the ablation generator (or other component) to determine, on a real time basis, the amount of energy to be supplied to the electrode(s) based on the temperature readings reported by a thermocouple, or other temperature reading device present.

In these above-described embodiments, by receiving the pulse rate data from the pulse rate detector and feedback mechanism after each successive ablation of the renal artery (or other tissue), the ablation system can determine the proper amount of energy to be supplied to the electrodes to attain the desired temperature range for the ablation. One skilled in the art will recognize based on the disclosure herein that it may be necessary to perform some additional calculations/experiments to determine the particular amount of energy to be transmitted to the electrode based, at least in part, on the pulse rate data gathered according to the present disclosure. These calculations/experiments may be used to prepare one or more suitable algorithms that may be used in the ablation catheter systems described herein to manage energy flow to the ablation catheter.

In an alternative embodiment of the present disclosure, after a baseline pulse rate has been determined as described above, the pulse rate of the patient may be measured continuously such that the operator (and generator or other component of the ablation system) has a continuous, uninterrupted stream of pulse rate data throughout a renal denervation procedure; that is, instead of monitoring the pulse rate data intermittently and periodically as described above, the pulse rate detector and feedback mechanism are continually active such that pulse rate data is continuously provided to the operator (and generator or other component of the ablation system) to determine the amount of energy that should be supplied to the electrode(s) to obtain the desired temperature at the site of the lesion-creation. In this embodiment, the energy of each subsequent ablation pulse, along with the pulse duration, can be increased or decreased depending upon the pulse rate of the patient as measured.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the disclosure, it is intended that all matter contained in the above description and shown in the accompanying drawings shall be interpreted as illustrative and not in a limiting sense.

What is claimed is:

1. An ablation catheter system for creating a lesion in a patient comprising an ablation catheter including at least one electrode, a generator, and a pulse rate detector and feedback mechanism in electrical connection with the generator, wherein the generator receives pulse rate data from the pulse rate detector via the feedback mechanism, and wherein the generator is configured to determine an amount of energy to be supplied to the at least one electrode based at least on the received pulse rate data to control and adjust a target temperature for the at least one electrode.

2. The ablation catheter system of claim 1 wherein the ablation catheter additionally includes at least one thermocouple.

3. The ablation catheter system of claim 1 wherein the pulse rate detector is sized and configured for attachment to the finger of a patient.

4. The ablation catheter system of claim 1 wherein the pulse rate detector is sized and configured for attachment to the wrist of a patient.

5. The ablation catheter system of claim 1 wherein the pulse rate detector is an electrocardiogram.

6. The ablation catheter system of claim 1 wherein the generator is a radio frequency generator.

7. The ablation catheter system of claim 1 wherein the feedback mechanism is in electrical connection with the generator through a computer.

8. The ablation catheter system of claim 1 wherein the ablation catheter includes at least two electrodes.

9. The ablation catheter system of claim 1 wherein the pulse rate detector is configured to continuously monitor the pulse rate of the patient.

* * * * *